(12) United States Patent
Vestgaarden (10) Patent No.: US 11,633,291 B2
(45) Date of Patent: Apr. 25, 2023

(54) INTERCONNECTED LOCKING PLATES FOR ADJACENT SPINAL VERTEBRAL BODIES

(71) Applicant: VGI Medical, LLC, Largo, FL (US)

(72) Inventor: Tov Inge Vestgaarden, Madeira Beach, FL (US)

(73) Assignee: VGI Medical, LLC, Largo, FL (US)

( * ) Notice: Subject to any disclaimer, the term of this patent is extended or adjusted under 35 U.S.C. 154(b) by 0 days.

(21) Appl. No.: 16/674,160

(22) Filed: Nov. 5, 2019

(65) Prior Publication Data

US 2020/0323642 A1 Oct. 15, 2020

Related U.S. Application Data

(63) Continuation of application No. 15/960,118, filed on Apr. 23, 2018, now Pat. No. 10,463,504, which is a
(Continued)

(51) Int. Cl.
*A61F 2/44* (2006.01)
*A61F 2/30* (2006.01)

(52) U.S. Cl.
CPC .... *A61F 2/447* (2013.01); *A61F 2002/30364* (2013.01); *A61F 2002/30433* (2013.01);
(Continued)

(58) Field of Classification Search
CPC ............ A61F 2/447; A61F 2002/30556; A61F 2002/30579; A61F 2002/30364;
(Continued)

(56) References Cited

U.S. PATENT DOCUMENTS 5,683,394 A 11/1997 Rinner
7,172,627 B2 2/2007 Fiere et al.
(Continued)

FOREIGN PATENT DOCUMENTS

WO WO 2011/028306 3/2011
WO WO 2013/043854 3/2013

OTHER PUBLICATIONS

Bolgova, M. V. et al., Age-Relaated Changes of Lumbar Vertebral Body Morphometry, Austin Journal of Anatomy, Aug. 2014, vol. 1, Issue 3, pp. 1-7.
(Continued)

*Primary Examiner* — Kevin T Truong
*Assistant Examiner* — Tracy L Kamikawa
(74) *Attorney, Agent, or Firm* — Pandiscio & Pandiscio (57) ABSTRACT

A device for insertion into a gap between adjacent, spaced apart bony elements includes an adjustable length interconnecting member having a distal and a proximal retention plate secured to opposite ends of the interconnecting member. The distal retention plate has a non-rotated position and a plurality of rotated positions. The non-rotated position aligns the distal retention plate with the gap prior to and during insertion of the distal retention plate into the gap. The distal retention plate is rotated after it has exited the gap on a distal side of the gap to prevent its return into the gap. The proximal retention plate is misaligned with the gap so that it cannot enter into the gap. The rotated distal retention plate cooperates with the proximal retention plate to hold bony elements such as adjacent vertebral bodies in a stable relationship to one another when the interconnecting member is shortened.

10 Claims, 6 Drawing Sheets

Related U.S. Application Data continuation of application No. 14/534,884, filed on Nov. 6, 2014, now abandoned, which is a continuation-in-part of application No. 13/238,524, filed on Sep. 21, 2011, now Pat. No. 10,555,821.

(52) U.S. Cl.
CPC .............. *A61F 2002/30471* (2013.01); *A61F 2002/30484* (2013.01); *A61F 2002/30538* (2013.01); *A61F 2002/30556* (2013.01); *A61F 2002/30576* (2013.01); *A61F 2002/30578* (2013.01); *A61F 2002/30579* (2013.01); *A61F 2002/30593* (2013.01); *A61F 2002/30616* (2013.01); *A61F 2002/30624* (2013.01); *A61F 2002/30777* (2013.01); *A61F 2002/30779* (2013.01); *A61F 2002/30785* (2013.01); *A61F 2002/30836* (2013.01); *A61F 2002/30841* (2013.01); *A61F 2002/30843* (2013.01); *A61F 2002/30904* (2013.01); *A61F 2250/0007* (2013.01); *A61F 2250/0065* (2013.01); *A61F 2310/00017* (2013.01); *A61F 2310/00023* (2013.01); *A61F 2310/00179* (2013.01)

(58) Field of Classification Search
CPC . A61F 2002/30841; A61F 2002/30904; A61B 17/7059
See application file for complete search history.

(56) References Cited

U.S. PATENT DOCUMENTS

| | | | |
|---|---|---|---|
| 7,621,938 | B2 | 11/2009 | Molz, IV |
| 7,662,186 | B2 | 2/2010 | Bagga et al. |
| 7,918,891 | B1 | 4/2011 | Curran et al. |
| 8,157,842 | B2 * | 4/2012 | Phan .................. A61B 17/7065 606/249 |
| 10,463,504 | B2 * | 11/2019 | Vestgaarden ........... A61F 2/447 |
| 2002/0161441 | A1 | 10/2002 | Lang et al. |
| 2003/0195632 | A1 | 10/2003 | Foley et al. |
| 2005/0159813 | A1 | 7/2005 | Molz, IV |
| 2007/0010889 | A1 | 1/2007 | Francis |
| 2008/0114456 | A1 | 5/2008 | Dewey et al. |
| 2008/0132949 | A1 | 6/2008 | Aferzon et al. |
| 2008/0161926 | A1 | 7/2008 | Melkent et al. |
| 2008/0183211 | A1 | 7/2008 | Lamborne et al. |
| 2008/0208344 | A1 * | 8/2008 | Kilpela .................. A61F 2/442 623/17.11 |
| 2008/0269898 | A1 | 10/2008 | Carls et al. |
| 2009/0187247 | A1 | 7/2009 | Metcalf, Jr. et al. |
| 2009/0234389 | A1 | 9/2009 | Chuang et al. |
| 2010/0241166 | A1 | 9/2010 | Dwyer et al. |
| 2010/0318127 | A1 | 12/2010 | Phan et al. |
| 2011/0166600 | A1 | 7/2011 | Lamborne et al. |
| 2012/0004729 | A1 * | 1/2012 | Zipnick .............. A61B 17/7065 623/17.16 |
| 2012/0221051 | A1 | 8/2012 | Robinson |
| 2012/0239089 | A1 | 9/2012 | Druma et al. |
| 2014/0324103 | A1 * | 10/2014 | Levieux ............. A61B 17/7047 606/248 |
| 2016/0367379 | A1 | 12/2016 | Refai |

OTHER PUBLICATIONS

Extended European Search Report for European Application No. 12833016, dated May 28, 2015.
International Search Report and Written Opinion of the International Searching Authority for International (PCT) Patent Application No. PCT/US2012/056304, dated Feb. 26, 2013.
International Preliminary Report on Patentability of the International Searching Authority for International (PCT) Patent Application No. PCT/US2012/056304, dated Apr. 3, 2014.

* cited by examiner

INTERCONNECTED LOCKING PLATES FOR ADJACENT SPINAL VERTEBRAL BODIES

CROSS-REFERENCE TO RELATED APPLICATIONS

This patent application is a continuation of pending prior U.S. patent application Ser. No. 15/960,118, filed Apr. 23, 2018 by VG Innovations, LLC for INTERCONNECTED LOCKING PLATES FOR ADJACENT SPINAL VERTEBRAL BODIES, which patent application is a continuation of prior U.S. patent application Ser. No. 14/534,884, filed Nov. 6, 2014 by VG Innovations, LLC for INTERCONNECTED LOCKING PLATES FOR ADJACENT SPINAL VERTEBRAL BODIES, which in turn is a continuation-in-part of pending prior U.S. patent application Ser. No. 13/238,524, filed Sep. 21, 2011 by Tov Inge Vestgaarden for METHOD AND APPARATUS FOR SPINAL INTERBODY FUSION INCLUDING FIXATION OR LOCKING PLATE.

The three (3) above-identified patent applications are hereby incorporated herein by reference.

BACKGROUND OF THE INVENTION

1. Field of the Invention

This invention relates to surgical methods and apparatus in general, and more particularly to surgical methods and apparatus for fusing spinal vertebral bodies.

2. Brief Description of the Related Art

In disc herniation, a spinal disc bulges from between two vertebral bodies and impinges on adjacent nerves, causing pain. In some cases, non-operative procedures such as bed rest, medication, lifestyle modifications, exercise, physical therapy, chiropractic care and steroid injections may suffice. However, in other cases, surgical intervention may be necessary. In cases where surgical intervention is prescribed, spinal vertebral body fusion may be desirable, i.e., the spine may have deteriorated so much that adjacent vertebral bodies must be fused together.

Spinal fixation is the current standard of care for surgically treating disc herniation in patients who have chronic pain and who have, or are likely to develop, associated spinal instability. Spinal fixation procedures are intended to relieve impingement on nerves by removing the portion of the disc or bone, or both, responsible for compressing the neural structures and destabilizing the spine.

The prior art teaches that excised disc or bone must be replaced with one or more intervertebral implants, or spacers, placed between adjacent vertebral bodies. These implants stabilize the adjacent vertebral bodies relative to one another so that the two vertebral bodies can fuse together.

The prior art considered as a whole at the time the present invention was made does not include any discussion concerning whether or not spinal fixation can be accomplished in the absence of a spinal fusion implant. It necessarily follows that it was not obvious to those of ordinary skill in the art at the time the present invention was made that spinal fixation could be accomplished in the absence of spinal fusion implants.

SUMMARY OF THE INVENTION

The long-standing but heretofore unfulfilled need for an improved spinal fusion implant is now met by a new, useful, and non-obvious invention.

The novel structure does not include a spinal fusion implant having a main body having a predetermined length, width, and thickness as disclosed in all prior art literature relating to spinal fusion implants.

However, the novel structure stops motion between adjacent vertebral bodies, thereby allowing fusion to occur. Conventional fusion accelerants, such as bone, are added to the empty space conventionally occupied by a spinal fusion implant main body in order to promote fusion.

The novel main body-less spinal fusion implant is inserted into a gap between adjacent, spaced apart vertebral bodies in a spinal joint, said gap created by surgical removal of a disc.

The novel spinal fusion implant includes an elongate interconnecting member that may have a fixed length or an adjustable length, a distal retention plate rotatably secured to a distal end of the interconnecting member, and a proximal retention plate secured to a proximal end of the interconnecting member.

The distal retention plate has an unrotated position of repose and an infinite plurality of rotated positions relative to said position of repose. Similarly, the proximal retention plate may have an unrotated position of repose and an infinite plurality of rotated positions relative to the position of repose.

When the distal and proximal retention plates are in their respective positions of repose, they are rotationally aligned with one another.

The proximal retention plate may be fixedly secured into its operable position so that it does not rotate relative to the interconnecting member but can be rotated conjointly with the interconnecting member.

The distal retention plate is in its position of repose when it is inserted into the surgically-created gap between adjacent vertebral bodies and is in a rotated position after the distal retention plate has cleared the distal surface of the spinal vertebral bodies, i.e., when the distal retention plate has passed through and is not positioned in said gap.

The distal retention plate when in the second position after said insertion abuts the superior and inferior vertebral bodies on the distal side of the spine and therefore prevents distal-to-proximal travel of the distal retention plate and thus prevents retraction of the interconnecting member from the gap and cooperates with the rotated proximal retention plate to hold adjacent vertebral bodies in a stable relationship to one another.

After the distal retention plate has cleared the distal spinal vertebral bodies and is rotated to prevent its re-entry into the gap, the interconnecting member is shortened to cause the proximal and distal retention plates to converge toward one another, thereby tightly sandwiching the adjacent vertebral bodies between them and holding said adjacent vertebral bodies against movement.

The rotation of the distal retention plate is preferably a ninety degree (90°) rotation relative to its position of repose, but the distal retention plate can still perform its function when rotated less than ninety degrees (90°) and such reduced angles of rotation are within the scope of this invention.

Both retention plates may have a roughened inboard surface to enhance their respective grips on their respective vertebral bodies.

Both retention plates may also have at least one protrusion formed on an inboard surface thereof to enhance their respective grips on their respective vertebral bodies.

The maximum length of the adjustable length interconnecting member is sufficient to span the proximal-to-distal extent of the gap and to allow the proximal and distal retention plates to be positioned outside the gap. The minimum length of the adjustable length interconnecting member is sufficient to enable the distal and proximal retention plates to tightly grip the adjacent vertebral bodies in sandwiched relation between them.

The proximal retention plate may be in its unrotated position of repose, rotationally aligned with the distal retention plate during distal retention plate insertion, or it may be rotated into its deployed configuration prior to insertion of the distal retention plate because the proximal retention plate does not enter into the gap.

The length of the interconnecting member is fixed or adjustable by any suitable mechanical means. The retention plates converge toward one another when the length of the interconnecting member is shortened, thereby holding the adjacent vertebral bodies in a stable relationship to one another as aforesaid.

The suitable mechanical means may include providing the interconnecting member in telescoping form.

As in the incorporated patent, the novel device does not require incisions on both sides of the spine, thereby obtaining an important object of the invention, i.e., providing a spinal fusion device that does not require incisions on both sides of a spine.

Another important object is to provide a spinal fusion device having no main body as in all prior art spinal fusion devices.

A more specific object is to provide a spinal fusion device that is inserted from a proximal side of a spine and which has a distal retention plate mounted on the distal end of an adjustable length interlocking member where the distal retention plate is aligned with a gap formed between adjacent vertebral bodies and inserted through said gap until the distal retention plate clears the distal edge of the adjacent vertebral bodies.

A closely related object is to provide a device that is inserted from a proximal side of a spine and which has a proximal retention plate mounted on the proximal end of an adjustable length interlocking member where the proximal retention plate may be aligned with the gap formed between adjacent vertebral bodies but which is not inserted into said gap.

Another closely related object is to provide a tool where distal and proximal retention plates are respectively mounted to distal and proximal ends of an adjustable length interconnecting member and where the distal retention plate is in a non-rotated position during insertion and in a rotated, deployed configuration after insertion.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

A spine includes a plurality of vertebral bodies separated by discs. A spine may deteriorate so much that adjacent vertebral bodies must be fused together. The novel spinal fusion implant is disposed between contiguous vertebral bodies to immobilize the affected segment of the spine and facilitate fusion between said adjacent vertebral bodies.

Prior art spinal fusion devices include a main body that substantially fills the gap between adjacent vertebral bodies. However, it has been discovered by the present inventor that fusion can occur in the absence of a main body. With a lower mass in the disc space, there is an increased chance, but no guarantee, of subsidence. Any structure with bleeding bone and micro motion will grow together. In this case the bleeding bone will grow to the distal and proximal plates where they attach to the vertebral bodies or directly between adjacent vertical bodies. If a surgeon adds autograft, allograft, or biologics to the disc space, this will be the traditional method of fusion.

The spine is prepared by removing some or all of the disc that resides in the space where the novel spinal fusion implant is to be inserted. The disc space is prepared with a rongeur or other surgical instrument, not depicted.

The novel structure effectively stabilizes the joint but permits the occurrence of "micro-motion" between the opposing vertebral bodies, which is important for successful bone fusion.

Figure 1:
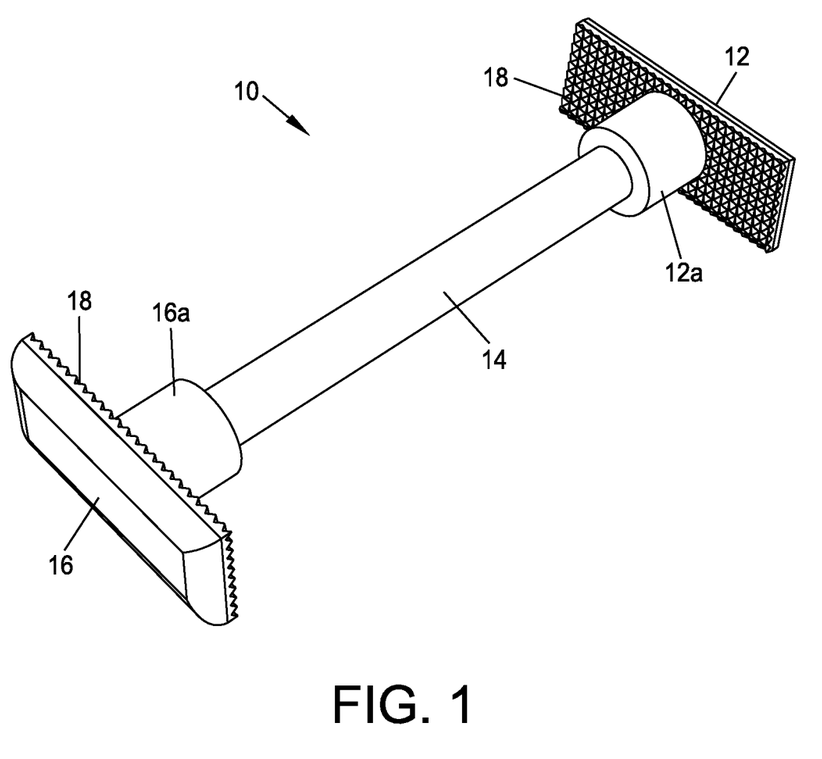
FIG. 1 is a perspective view of a first embodiment of the invention.
Figure 2:
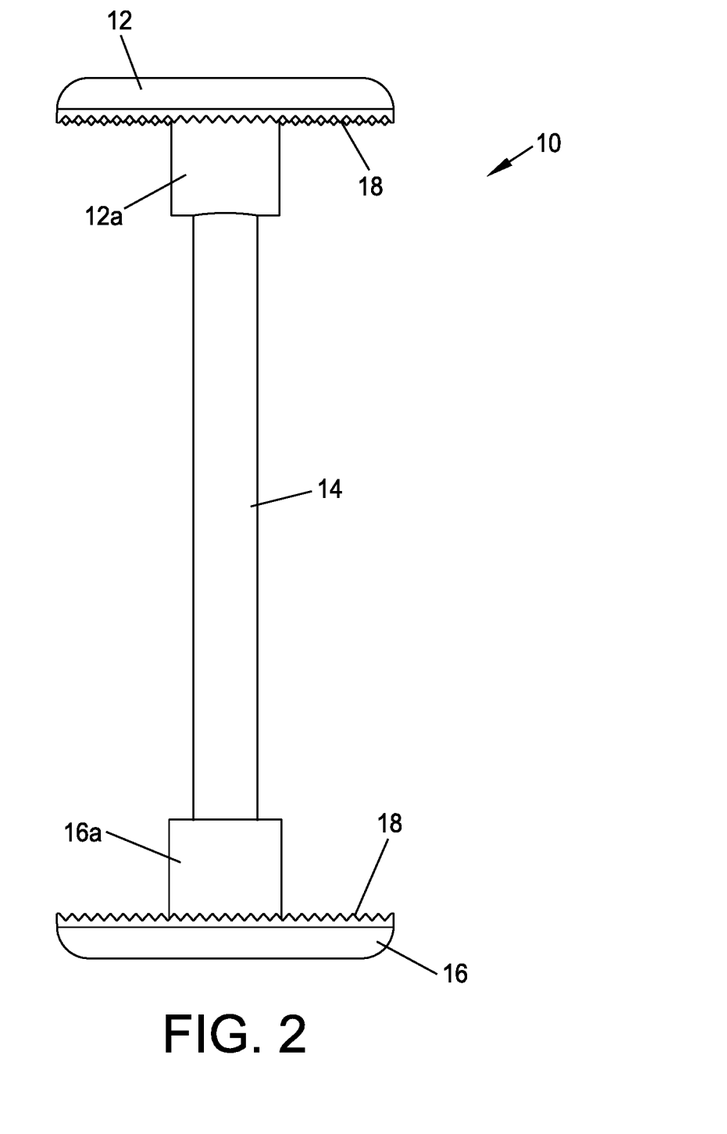
FIG. 2 is a top plan view thereof.
Figure 3:
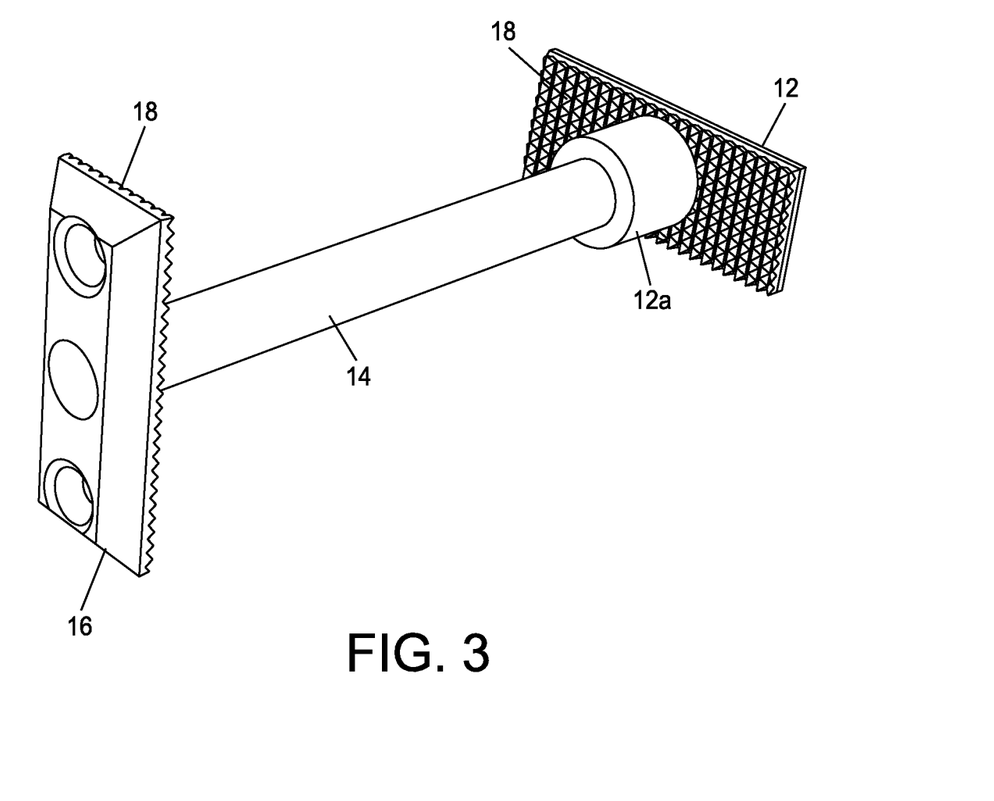
FIG. 3 is a perspective view of a second embodiment.

Referring now to FIGS. 1-3, novel tool 10 includes distal retention plate 12 which is attached to the distal end of elongate interconnecting member 14. Proximal retention plate 16 is attached to the proximal end of said elongate interconnecting member 14. Proximal retention plate 16 may be mounted for relative rotation with respect to interconnecting member 14 or it may be fixedly secured thereto or integrally formed therewith for conjoint rotation therewith.

Boss 12*a* may be formed integrally with distal retention plate 12 and boss 16*a* may be formed integrally with proximal retention plate 16, said bosses receiving the opposite ends of interconnecting member 14 to enhance the structural integrity of the novel structure. There is no relative rotation and no longitudinal displacement between the bosses and said opposite ends.

In the embodiments of FIGS. 1-3, rotation of proximal retention plate 16 by a surgeon effects conjoint rotation of distal retention plate 12. Said plates may be in rotational alignment with one another in a first embodiment as depicted in FIGS. 1 and 2, or they may be rotated ninety degrees (90°) with respect to one another in a second embodiment as depicted in FIG. 3. Other angular orientations between the retention plates are within the scope of this invention.

The first embodiment of this invention as illustrated is a non-telescoping embodiment. All other embodiments have telescopically interconnected parts. The first embodiment could also be modified so that the distal and proximal plates could be telescopically interconnected to one another.

As shown in FIG. 3, proximal retention plate 16 has at least two (2) openings that receive screws so that plate 16 may be secured to the vertebral bodies.

Each retention plate preferably has a roughened inboard surface as at 18. The inboard surface is the surface that abuts the patient's body. At least one protuberance may also be formed in the respective inboard surfaces of distal and proximal retention plates 12 and 16, respectively. Such protuberances would perform the same gripping function as the aforesaid roughened surfaces. The use of only one (1) protrusion is within the scope of this invention and is considered the equivalent of a roughened surface.

Figure 4:
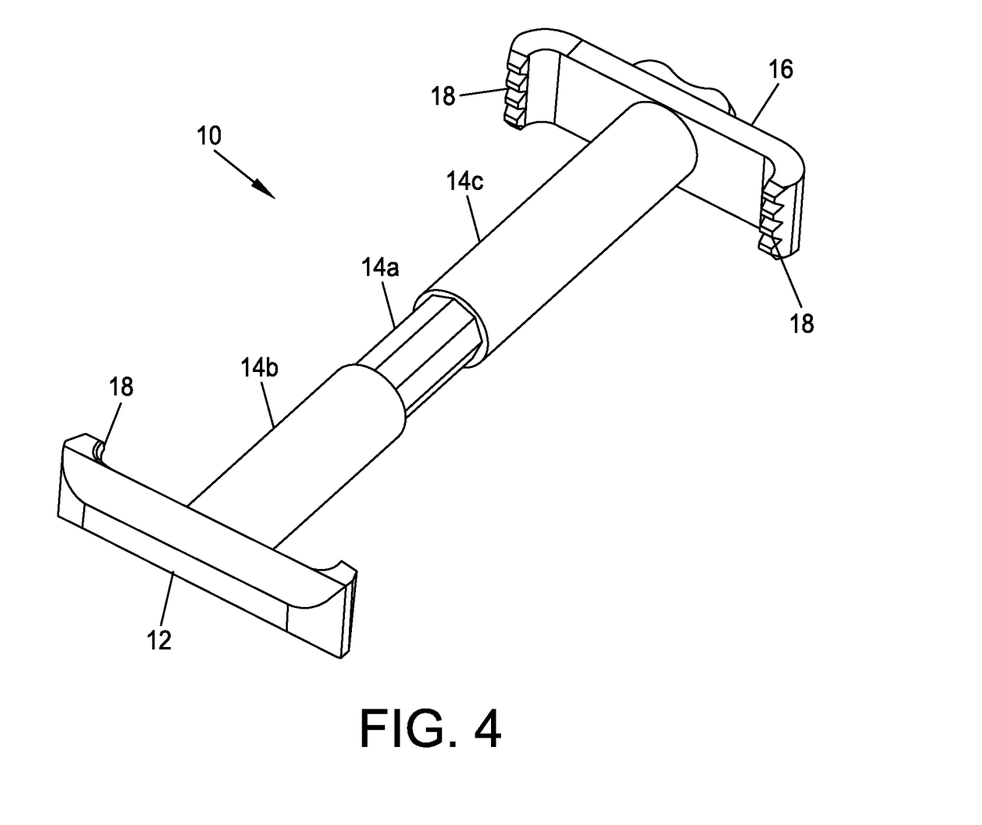
FIG. 4 is a perspective view of a third embodiment.

FIG. 4 depicts a third embodiment. Retention plates 12 and 16 in this embodiment have a square bracket ([) shape with rounded corners and the retention plates 12, 16 contact the patient's body only at the inboard-projecting opposite ends of such retention plates. The body-contacting opposite ends have roughened surfaces 18 similar to the roughened surfaces of the first embodiment.

Elongate interconnecting member 14 in this embodiment has three parts, i.e., elongate base 14a having an octagonal transverse cross-section, distal part or sleeve 14b which is formed integrally with or fixedly secured to distal retention plate 12 for conjoint rotation therewith, and proximal part or sleeve 14c which is formed integrally with or fixedly secured to proximal retention plate 16 for conjoint rotation therewith.

Parts 14b and 14c are provided with octagonal lumens that telescopically mate with elongate base 14a. A surgeon may insert distal retention plate 12 through the disc space until said distal retention plate clears the vertebrae while holding proximal retention plate 16 in the position depicted in FIG. 4. Rotation of proximal retention plate 16 then effects conjoint rotation of distal retention plate 12 just as in the first three embodiments. The difference is that said retention plates of this second embodiment are telescopically interconnected so that tool 10 can be used with patients of varying sizes. Thus it is understood that the transverse cross-section of base 14a and the mating lumens of parts 14b and 14c could be of any non-round cross-section.

Figure 5:
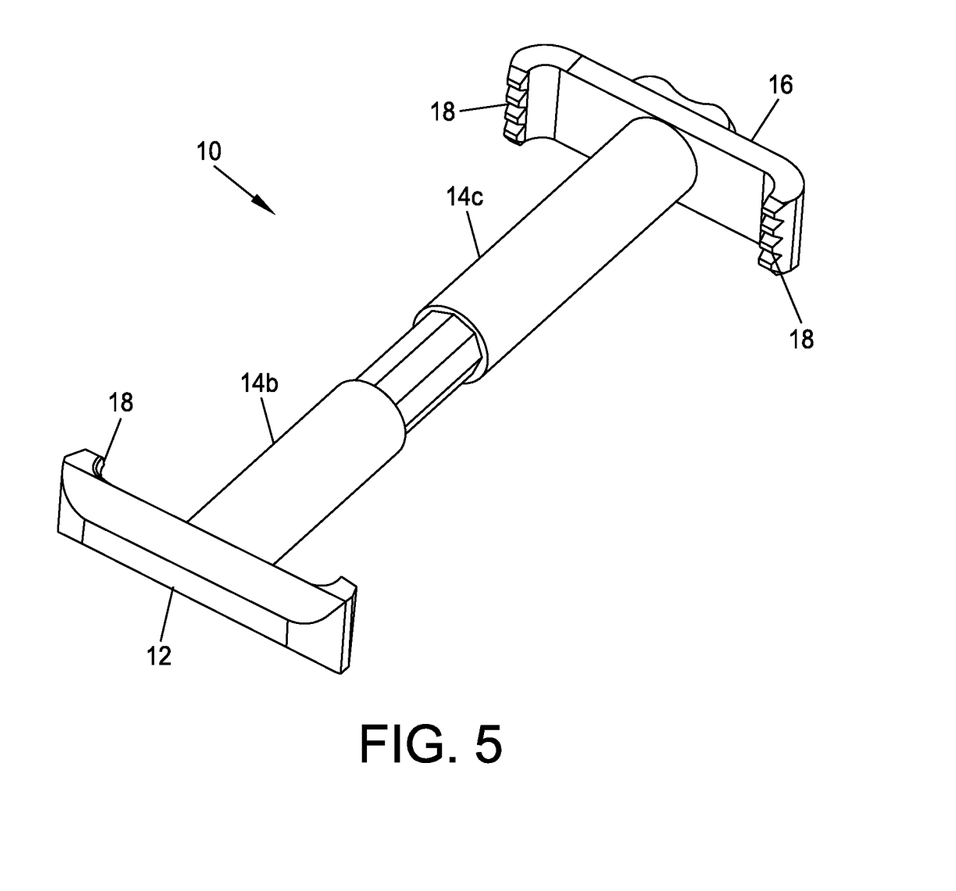
FIG. 5 is a perspective view of a fourth embodiment.

A fourth embodiment is depicted in FIG. 5. This embodiment eliminates base member 14a. Distal and proximal parts 14b, 14c telescopically engage one another. More particularly 14c has an internal lumen designed to accept the cross-sectional shape of 14b.

Figure 6:
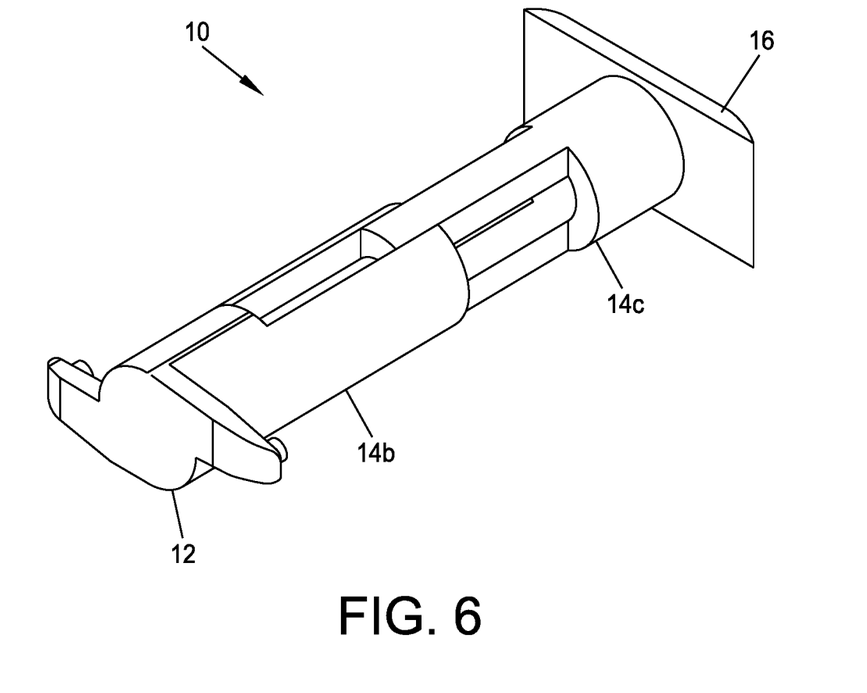
FIG. 6 is a perspective view of a fifth embodiment.

A fifth embodiment is depicted in FIG. 6. This embodiment also eliminates base member 14a. Distal and proximal parts 14b, 14c telescopically engage one another. More particularly, each part 14b, 14c has two diametrically oposed arms and two diametrically oposed slots so that the arms of distal part 14b slidingly engage the slots of proximal part 14c and the arms of proximal part 14c slidingly engage the slots of distal part 14b.

Distal retention plate 12 in FIG. 6 has a different structure than proximal retention plate 16 to allow plate 12 to cut through surrounding soft tissue.

Misalignment (at least some rotation) of distal retention plate 12 from its non-rotated position limits motion in a multi-directional joint. More particularly, the shape of the main body in the incorporated disclosure limits motion in flexion/extension, while distal retention plate 12 in cooperation with proximal retention plate 16 limits lateral bending. Accordingly, this main body-less embodiment does not limit motion in flexion/extension.

Thus it is understood that the spine is locked in sandwiched relation between proximal retention plate 16 on the proximal side and distal retention plate 12 on the distal side even though only one incision has been made, said incision being on said proximal side, thereby distinguishing the invention from prior art tools and methods that require two (2) incisions, i.e., incisions on both the proximal and the distal side of the spine.

Spinal fusion implant 10 is inserted into a disc space using a lateral approach. The lateral approach is preferred because it is familiar to spine surgeons, and also minimizes the possibility of damage to the spinal cord during insertion of the tool.

Although tool 10 has been disclosed in the context of fusing an intervertebral joint, it may also be used to stabilize and fuse any joint having an anatomy similar to an intervertebral joint, i.e., a pair of opposing bony surfaces defining a gap therebetween. By way of example and not limitation, the novel tool may be used in small joints as in the finger, toe, etc.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A device for securing a first vertebral body to a second vertebral body, wherein:

the first vertebral body comprises an inferior end plate, a superior end plate, a distal outer surface and a proximal outer surface, wherein the distal outer surface and the proximal outer surface of the first vertebral body extend generally perpendicular to the inferior end plate and the superior end plate of the first vertebral body;

wherein the second vertebral body comprises an inferior end plate, a superior end plate, a distal outer surface and a proximal outer surface, wherein the distal outer surface and the proximal outer surface of the second vertebral body extend generally perpendicular to the inferior end plate and the superior end plate of the second vertebral body;

wherein the superior end plate of the first vertebral body and the inferior end plate of the second vertebral body are separated by a gap; and wherein the distal outer surface of the first vertebral body is generally aligned with the distal outer surface of the second vertebral body, and wherein the proximal outer surface of the first vertebral body is generally aligned with the proximal outer surface of the second vertebral body, said device comprising:

a distal retention plate characterized by a long dimension, a short dimension, a first proximal bearing surface portion and a second proximal bearing surface portion, said distal retention plate having an elongate shaft secured in normal relation thereto; and a proximal retention plate characterized by a long dimension, a short dimension, a first distal bearing surface portion and a second distal bearing surface portion, said proximal retention plate having an elongate shaft secured in normal relation thereto;

said elongate shaft of said distal retention plate being assembled in telescoping relation to said elongate shaft of said proximal retention plate, with:

(i) said distal retention plate and said proximal retention plate being in rotationally fixed disposition relative to one another so that said long dimension of said distal retention plate extends parallel to said long dimension of said proximal retention plate, and (ii) said distal retention plate and said proximal retention plate being in longitudinally adjustable disposition relative to one another so that a distance between said first proximal bearing surface portion of said distal retention plate and said first distal bearing surface portion of said proximal retention plate, and a distance between said second proximal bearing surface portion of said distal retention plate and said second distal bearing surface portion of said proximal retention plate, are selectively adjustable;

and further wherein said device is constructed so as to be capable of selectively assuming the following dispositions:

(a) an insertion disposition in which said distal retention plate is disposed such that said long dimension of said distal retention plate is configured to extend generally parallel to a distal edge of the first vertebral body between the distal outer surface and the superior end plate of the first vertebral body;

(b) a rotated disposition in which (i) said distal retention plate is disposed such that said short dimension of said distal retention plate is configured to extend generally parallel to the distal edge of the first vertebral body between the distal outer surface and the superior end plate of the first vertebral body, and (ii) the distance between said first proximal bearing surface portion of said distal retention plate and said first distal bearing surface portion of said proximal retention plate is greater than a distance between the distal outer surface of the first vertebral body and the proximal outer surface of the first vertebral body, and the distance between said second proximal bearing surface portion of said distal retention plate and said second distal bearing surface portion of said proximal retention plate is greater than a distance between the distal outer surface of the second vertebral body and the proximal outer surface of the second vertebral body; and (c) a secured disposition in which (i) said distal retention plate is disposed such that said short dimension of said distal retention plate is configured to extend generally parallel to the distal edge of the first vertebral body between the distal outer surface and the superior end plate of the first vertebral body, and (ii) the distance between said first proximal bearing surface portion of said distal retention plate and said first distal bearing surface portion of said proximal retention plate is the same as or less than the distance between the distal outer surface of the first vertebral body and the proximal outer surface of the first vertebral body, and the distance between said second proximal bearing surface portion of said distal retention plate and said second distal bearing surface portion of said proximal retention plate is the same as or less than the distance between the distal outer surface of the second vertebral body and the proximal outer surface of the second vertebral body.

2. The device of claim 1, wherein:
each of said distal retention plate and said proximal retention plate are sufficiently large to span a distance of the gap between the superior end plate of the first vertebral body and the inferior end plate of the second vertebral body when rotated after insertion.

3. The device of claim 2, wherein:
said elongate shafts comprise a combined length configured to enable said proximal retention plate and said distal retention plate to extend beyond (i) the proximal outer surface of the first vertebral body and the proximal outer surface of the second vertebral body, and (ii) the distal outer surface of the first vertebral body and the distal outer surface of the second vertebral body, respectively.

4. The device of claim 2, wherein said distal retention plate of said device comprises an infinite plurality of rotated positions relative to a position of said distal retention plate when said device is in said insertion disposition.

5. The device of claim 4, wherein:
in said insertion disposition said device is configured to be aligned with the gap between the superior end plate of the first vertebral body and the inferior end plate of the second vertebral body prior to insertion and during insertion of said device into the gap;

said device being in said a rotated disposition after said distal retention plate has exited the gap on a distal side of the gap, but prior to said proximal retention plate entering the gap;

said device when in said rotated disposition is configured to prevent distal-to-proximal or proximal-to-distal displacement of said retention plates into the gap; and when said device is in said secured disposition, said distal retention plate is configured to cooperate with said proximal retention plate to hold the first vertebral body and the second vertebral body in a stable relationship to one another.

6. The device of claim 5, wherein:
said telescoping relation is configured to enable retraction of the elongate shafts to thereby enable the proximal and distal retention plates to positively engage the first vertebral body and the second vertebral body.

7. The device of claim 2, wherein at least one of said first proximal bearing surface portion of said distal retention plate, said second proximal bearing surface portion of said distal retention plate, said first distal bearing surface portion of said proximal retention plate, and said second distal bearing surface portion of said proximal retention plate comprises a roughened surface.

8. The device of claim 2, further comprising;
said proximal retention plate having screw-receiving holes formed therein configured to enable screws to fasten the proximal retention plate to said first and second vertebral bodies.

9. The device of claim 1, further comprising:
each of said elongate shafts having a non-round transverse cross-section;
said distal retention plate elongate shaft having a non-round lumen that telescopically mates with a non-round transverse cross-section of said proximal retention plate elongate shaft;
whereby rotation of said proximal retention plate effects conjoint rotation of said distal retention plate.

10. The device of claim 1, further comprising:
each of said elongate shafts having a non-round transverse cross-section;
said proximal retention plate elongate shaft comprising a sleeve having a non-round lumen that telescopically mates with a non-round transverse cross-section of said distal retention plate elongate shaft;
whereby rotation of said proximal retention plate effects conjoint rotation of said distal retention plate.

* * * * *